United States Patent
Padiy

(10) Patent No.: US 9,410,854 B2
(45) Date of Patent: Aug. 9, 2016

(54) METHODS AND DEVICES FOR MEASURING CORE BODY TEMPERATURE

(75) Inventor: Alexander V. Padiy, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 627 days.

(21) Appl. No.: 12/531,313

(22) PCT Filed: Feb. 15, 2008

(86) PCT No.: PCT/IB2008/050567
§ 371 (c)(1),
(2), (4) Date: Sep. 15, 2009

(87) PCT Pub. No.: WO2008/110949
PCT Pub. Date: Sep. 18, 2008

(65) Prior Publication Data
US 2010/0113894 A1    May 6, 2010

Related U.S. Application Data

(60) Provisional application No. 60/894,916, filed on Mar. 15, 2007.

(51) Int. Cl.
*A61B 5/01* (2006.01)
*G01K 13/00* (2006.01)
(Continued)

(52) U.S. Cl.
CPC ............ *G01K 13/002* (2013.01); *A61B 5/0002* (2013.01); *A61B 5/015* (2013.01); *A61B 5/6814* (2013.01); *A61B 5/6815* (2013.01); *A61B 5/6833* (2013.01); *A61B 5/6838* (2013.01);

(Continued)

(58) Field of Classification Search
CPC .......... A61B 2562/0271; G01K 1/026; G01K 13/002
USPC ......................................................... 600/549
See application file for complete search history.

(56) References Cited

U.S. PATENT DOCUMENTS 3,933,045 A    1/1976  Fox et al.
5,673,692 A    10/1997 Schulze et al.
(Continued)

FOREIGN PATENT DOCUMENTS

CA    2444490 A1    12/2002
CA    2538940 A1    6/2006
(Continued)

*Primary Examiner* — Rene Towa
*Assistant Examiner* — H. Q. Nguyen

(57) ABSTRACT

A core body temperature measurement device includes a plurality of electronic temperature sensors (12, 12f, 12b, 132) operatively coupled with or near a surface (STA, PAA, BTT) having a surface temperature approximating the core body temperature, and a readout controller (10, 48, 68, 90, 124) including a maximum temperature reading selector (14). The readout controller is configured to acquire temperature readings using the plurality of temperature sensors and to output a core body temperature based on a highest usable temperature reading of the acquired temperature readings as determined by the maximum temperature reading selector. A core body temperature measurement method includes: acquiring a plurality of temperature readings at and near a surface (STA, PAA, BTT) having a surface temperature approximating the core body temperature; generating a highest usable temperature reading from the acquired temperature readings; and outputting a core body temperature based on the highest usable temperature.

12 Claims, 9 Drawing Sheets

Figure 1:
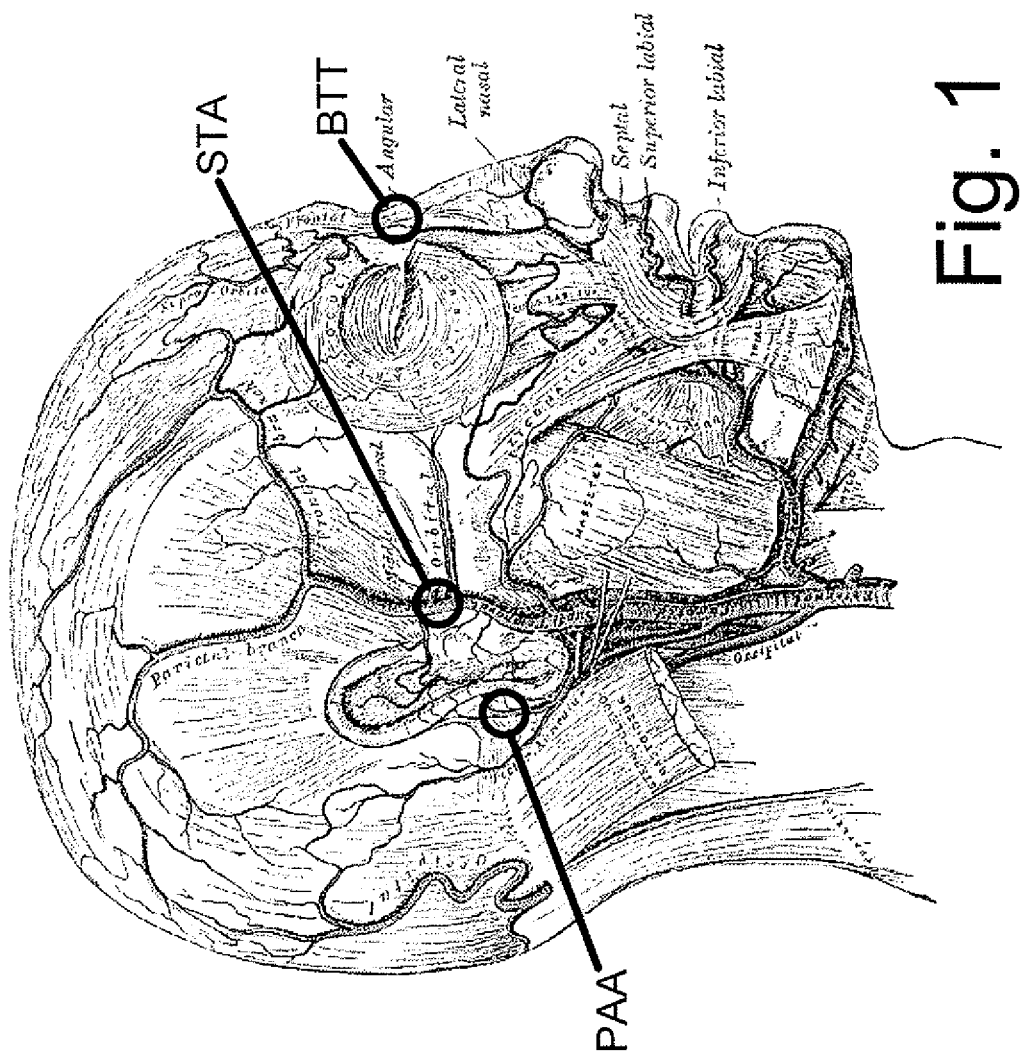

(51) Int. Cl.
*A61B 5/00* (2006.01)
*G01K 1/02* (2006.01)
*G01K 1/16* (2006.01)
*G01K 7/42* (2006.01)
*A61B 5/145* (2006.01)

(52) U.S. Cl.
CPC ........ *G01K 1/026* (2013.01); *G01K 1/16* (2013.01); *G01K 7/42* (2013.01); *A61B 5/145* (2013.01); *A61B 5/4064* (2013.01); *A61B 2562/0271* (2013.01)

(56) References Cited

U.S. PATENT DOCUMENTS

| | | | |
|---|---|---|---|
| 5,816,706 A | 10/1998 | Heikkila et al. | |
| 6,886,978 B2 | 5/2005 | Tokita et al. | |
| 2002/0143257 A1 | 10/2002 | Newman et al. | |
| 2003/0099082 A1* | 5/2003 | Tuo et al. | 361/290 |
| 2004/0059212 A1 | 3/2004 | Abreu | |
| 2004/0242976 A1 | 12/2004 | Abreu | |
| 2004/0243021 A1* | 12/2004 | Murphy et al. | 600/549 |
| 2005/0113654 A1 | 5/2005 | Weber et al. | |
| 2005/0209516 A1 | 9/2005 | Fraden | |
| 2005/0271117 A1 | 12/2005 | Grassl et al. | |
| 2006/0100530 A1 | 5/2006 | Kliot et al. | |
| 2006/0189883 A1 | 8/2006 | Pomfrett et al. | |
| 2006/0189884 A1 | 8/2006 | Lussier et al. | |
| 2007/0237204 A1* | 10/2007 | Kwon et al. | 374/163 |
| 2009/0105605 A1* | 4/2009 | Abreu | 600/549 |

FOREIGN PATENT DOCUMENTS

| | | |
|---|---|---|
| EP | 0310101 A2 | 4/1989 |
| JP | 59103234 A | 6/1984 |
| RU | 2256397 C1 | 7/2005 |
| WO | 0016051 A1 | 3/2000 |
| WO | 03001167 A2 | 1/2003 |
| WO | 04001373 A2 | 12/2003 |

\* cited by examiner

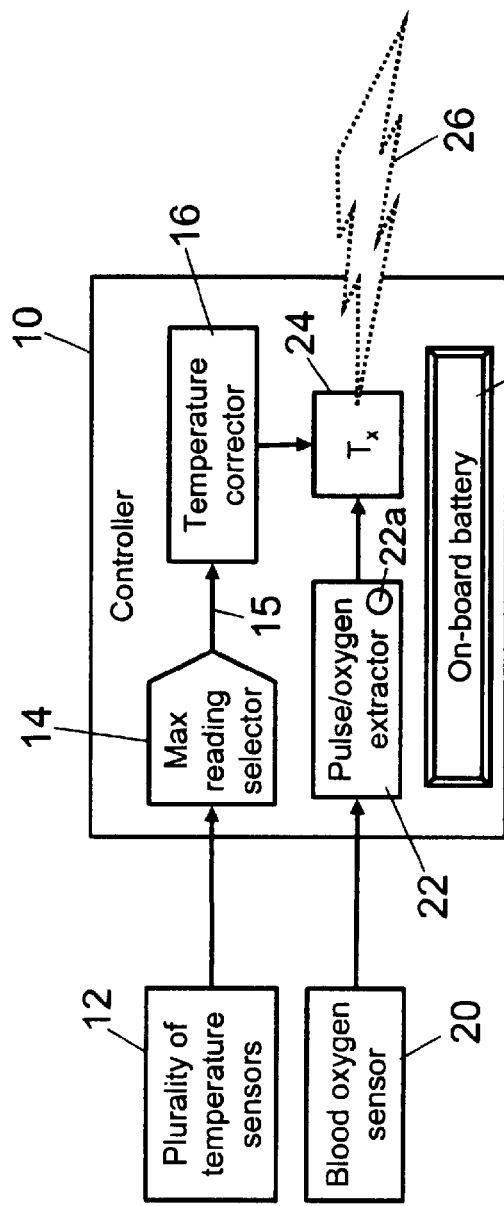
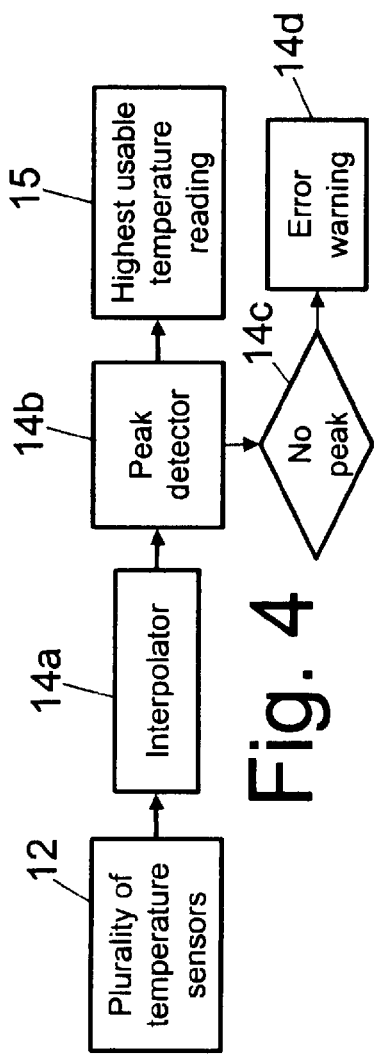
Fig. 3
Fig. 4

METHODS AND DEVICES FOR MEASURING CORE BODY TEMPERATURE

CROSS REFERENCE TO RELATED APPLICATIONS

This application claims the benefit of U.S. provisional application Ser. No. 60/894,916 filed Mar. 15, 2007, which is incorporated herein by reference.

The following relates to the medical arts. It finds particular application in measuring core body temperature, and is described with particular reference thereto. However, the following finds more general application in measuring core body temperature-related values suitable for use in medical diagnostic, treatment monitoring, and related medical applications.

Core body temperature is an important medical vital sign. Unlike other vital signs such as heart rate or blood pressure, core body temperature is relatively insensitive to variations due to psychological or emotional state. Thus, core body temperature can be a good indicator of a medical problem. Moreover, a shift in core body temperature of only a few degrees Celsius away from the typical range can be life-threatening in and of itself, providing further motivation for monitoring this critical vital sign.

Unfortunately, core body temperature has heretofore been more difficult to measure than other vital signs such as heart rate or blood pressure. The core body temperature is defined as the temperature of blood flowing through the heart. However, for clinical purposes the core body temperature is typically taken as the brain temperature, since this value is typically close to the cardiac core temperature, and elevated brain temperature is a clinically serious condition that would be useful to monitor in clinical settings. As used herein, core body temperature is taken to correspond to the brain temperature. A rectal thermometer is also sometimes used to measure core body temperature, under the assumption that the rectal temperature is a suitable surrogate for the core body temperature. However, rectal temperature may differ substantially from core body temperature of the heart or brain. Insertion of a rectal thermometer is also uncomfortable for the patient, and rectal thermometry is not well-suited for extended monitoring over a period of hours, days, or longer.

To precisely measure core body temperature, a temperature sensor can be inserted into brain vasculature using a suitable catheter instrument. Although precise, this approach is clinically problematic because it is invasive and can produce disadvantageous side effects such as infection, vascular clotting, or so forth.

Core body temperature can also be estimated by measuring forehead temperature. This is the basis for the home diagnostic of placing a hand over the forehead of the patient to determine whether a fever is present. As a measure of core body temperature, this technique is inexact at best. A more precise core body temperature estimate can be obtained by placing a thermocouple, thermistor, or other electronic temperature sensor into contact with the forehead. However, the temperature acquired by such sensors can differ substantially from the core body temperature due to temperature drop across the skin and other intervening tissue. This temperature drop is not constant, but varies significantly as a function of sweat, room temperature, and other factors. The acquired temperature can also vary depending upon at what position on the forehead the sensor is placed.

Core body temperature is also sometimes estimated using an oral thermometer. It is known that placement of the thermometer in a posterior sublingual pocket provides a relatively accurate estimate of core body temperature, as this region is close to substantial arterial structure. However, even small errors in the positioning of the oral temperature can result in a substantial error in the temperature reading. Respiration, ingestion, or other oral activities can also adversely affect the temperature reading.

Thermometers are also known which are inserted into the ear canal to contact the tympanic membrane, also known colloquially as the ear drum. The tympanic membrane has relatively close proximity to the brain and reflects the core body temperature relatively accurately. However, the shape of the ear canal varies from person to person, and in some instances access to the tympanic membrane may be impeded or blocked by curvature of the ear canal. Another potential source of error is wax buildup in the ear canal. Physical contact with the tympanic membrane by the thermometer can also promote ear infection, which can be a serious medical condition. Core body temperature measurement via the tympanic membrane is also not well suited for extended monitoring over a period of hours, days, or longer.

Abreu, U.S. Published Application 2004/0059212, discloses a recently developed technique for measuring core body temperature that overcomes some of these difficulties. The approach of Abreu is based on identification of a thermally conductive pathway to the brain, called a "brain tunnel" in US 2004/0059212, located between the eyes proximate to an orbit or eye socket. By using contact thermometry at the location of this "brain tunnel," a relatively accurate core body temperature reading can be non-invasively obtained. Unfortunately, the identified brain tunnel has a small external cross-section near the eye orbit, which makes the accuracy of the core body temperature measurement strongly dependent upon precise placement of the temperature sensor. Positional deviations of as little as one or two millimeters can adversely affect the core body temperature measurement via the brain tunnel.

While acquisition of an accurate core body temperature reading is difficult, extended monitoring of this vital sign is more difficult still. As noted above, suitable sites for measuring core body temperature, such as the posterior sublingual pocket and the "brain tunnel" identified by Abreu, are typically small. As a result, shift or movement of the temperature sensor over time during extended monitoring is problematic.

The following provides new and improved apparatuses and methods which overcome the above-referenced problems and others.

In accordance with one aspect, a core body temperature measurement device includes a plurality of electronic temperature sensors operatively coupled with or near a surface having a surface temperature approximating the core body temperature, and a readout controller including a maximum temperature reading selector. The readout controller is configured to acquire temperature readings using the plurality of temperature sensors and to output a core body temperature based on a highest usable temperature reading of the acquired temperature readings as determined by the maximum temperature reading selector, optionally also including a correction for the temperature drop through the skin as will be described in more detail in the sequel.

In accordance with another aspect, a core body temperature measurement device includes at least one electronic temperature sensor operatively coupled with or near a surface having a surface temperature approximating the core body temperature, and a readout controller configured to acquire an input temperature reading from the at least one electronic temperature sensor and to obtain a core body temperature therefrom. The readout controller includes a temperature corrector that increases the input temperature reading to account for a temperature difference between the input temperature reading and the core body temperature.

In accordance with another aspect, a core body temperature measurement method includes: acquiring a plurality of temperature readings at and near a surface having a surface temperature approximating the core body temperature; generating a highest usable temperature reading from the acquired temperature readings; and outputting a core body temperature based on the highest usable temperature.

One advantage resides in providing an accurate non-invasive core body temperature measurement.

Another advantage resides in providing a non-invasive core body temperature measurement that is relatively insensitive to the precise positioning of the temperature measurement device.

Another advantage resides in providing a non-invasive core body temperature measurement that is corrected for a temperature difference between the surface at which the temperature is measured and the body core.

Still further advantages of the present invention will be appreciated to those of ordinary skill in the art upon reading and understand the following detailed description.

FIG. 1 diagrammatically shows a side view of a human head with the skin and other outer tissue removed to reveal arteries of the right side of the face and scalp, and further indicating preferred locations for acquiring non-invasive core body temperature measurements.

Figure 2:
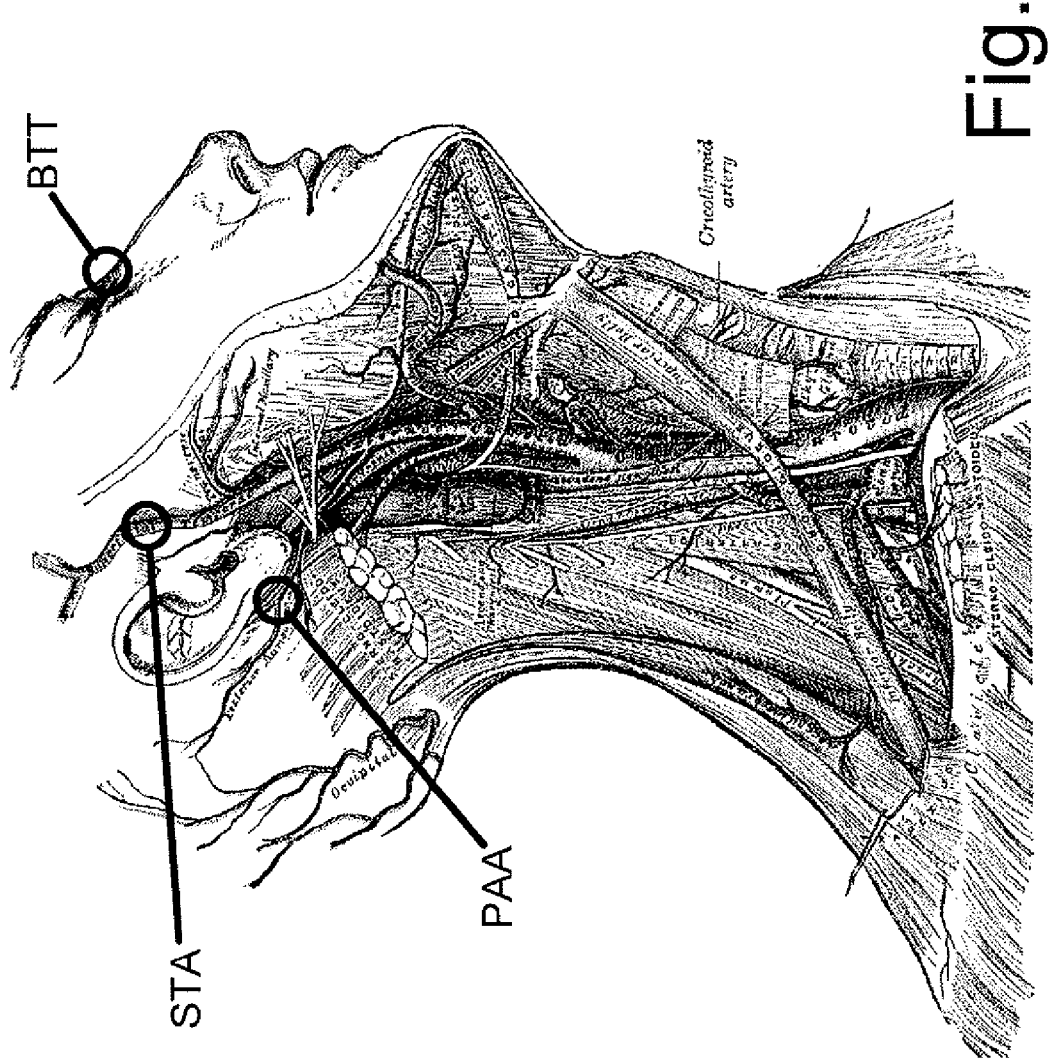

FIG. 2 diagrammatically shows a side view of a human neck supporting a partially turned human head, with the skin and other outer tissues partially removed to reveal arteries of the right side of the neck and head, and further indicating preferred locations for acquiring non-invasive core body temperature measurements.

FIG. 3 diagrammatically shows a readout controller for a core body temperature measurement device.

FIG. 4 diagrammatically shows a maximum temperature reading selector.

Figure 5:
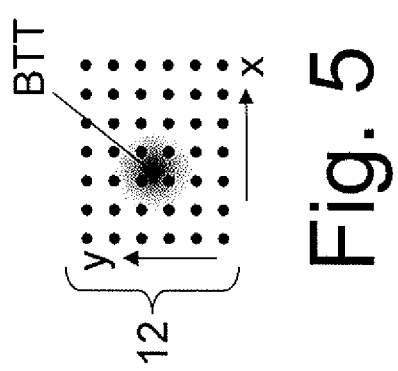

FIG. 5 diagrammatically shows an array of temperature sensors encompassing a brain tunnel location.

Figure 6:
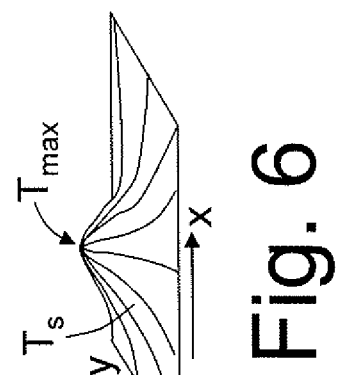

FIG. 6 diagrammatically shows an interpolated temperature reading surface acquired by the array of temperature sensors positioned as shown in FIG. 5.

Figure 7:
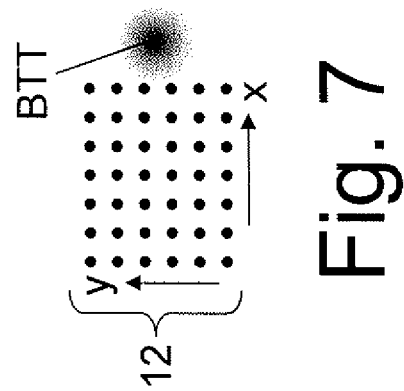

FIG. 7 diagrammatically shows an array of temperature sensors to the left of a brain tunnel location.

Figure 8:
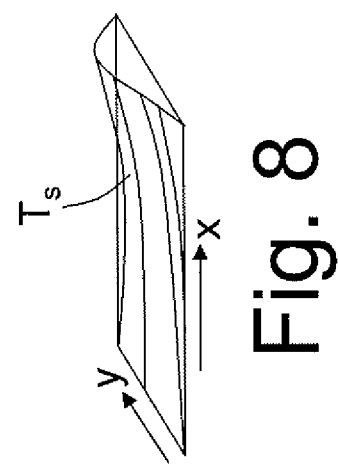

FIG. 8 diagrammatically shows an interpolated temperature reading surface acquired by the array of temperature sensors positioned as shown in FIG. 8.

Figure 9:
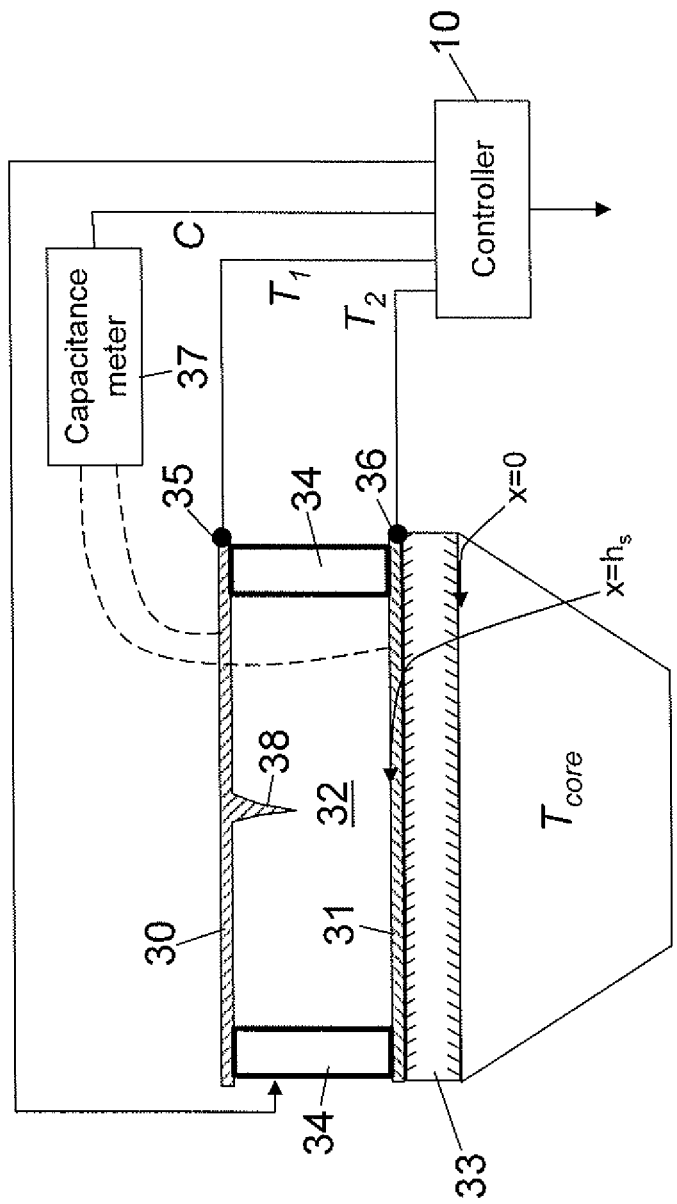

FIG. 9 diagrammatically shows a combination temperature/heat flux sensor.

Figure 10:
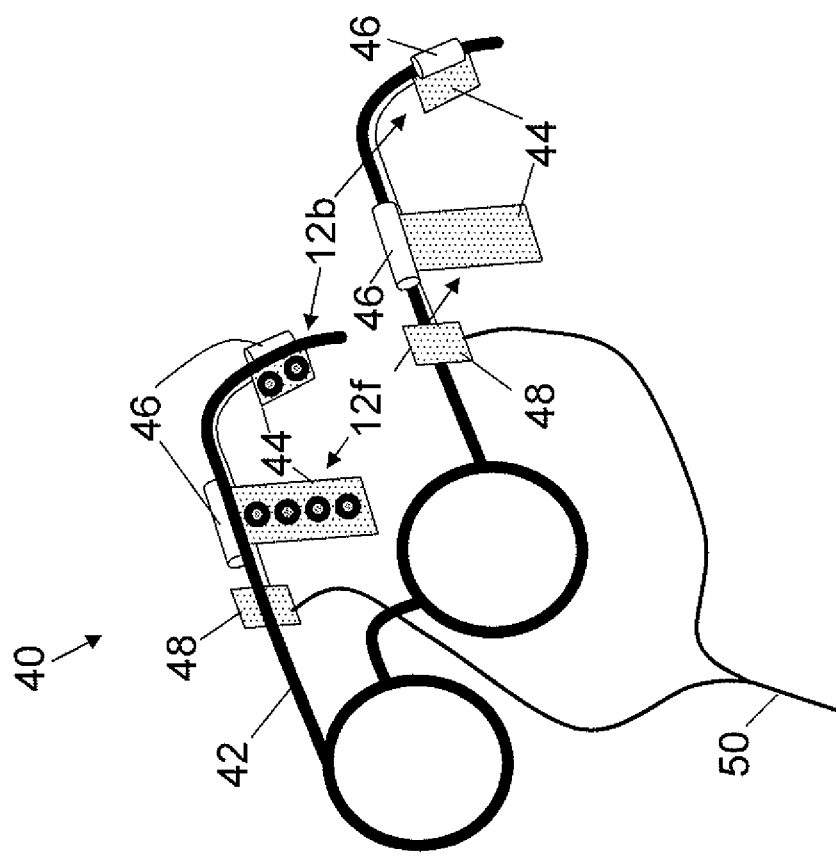

FIG. 10 diagrammatically shows a core body temperature measurement device including a mechanical frame in the form of an eyeglasses frame.

Figure 11:
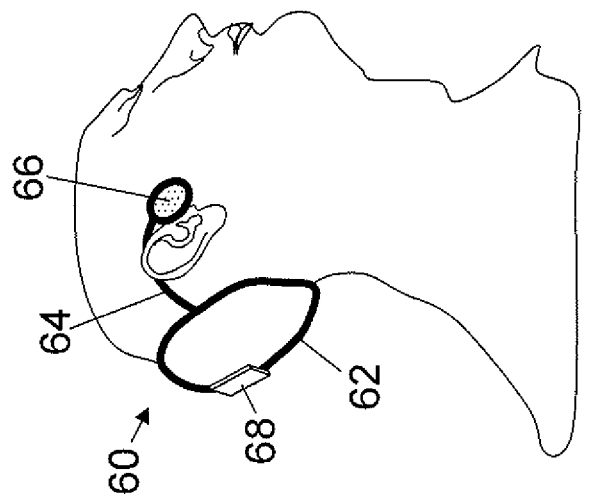

FIG. 11 diagrammatically shows a core body temperature measurement device including a mechanical frame in the form of a behind-the-head pillow having extensions configured to loop over the left and right auricles.

Figure 12:
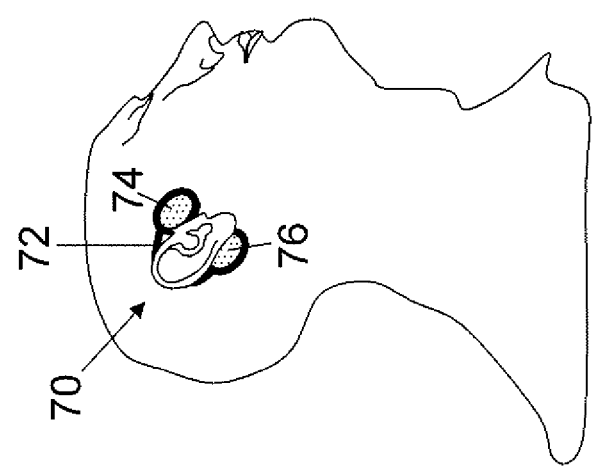

FIG. 12 diagrammatically shows a core body temperature measurement device including a mechanical frame in the form of headset including an earloop disposed around a proximate auricle without a headband.

Figure 13:
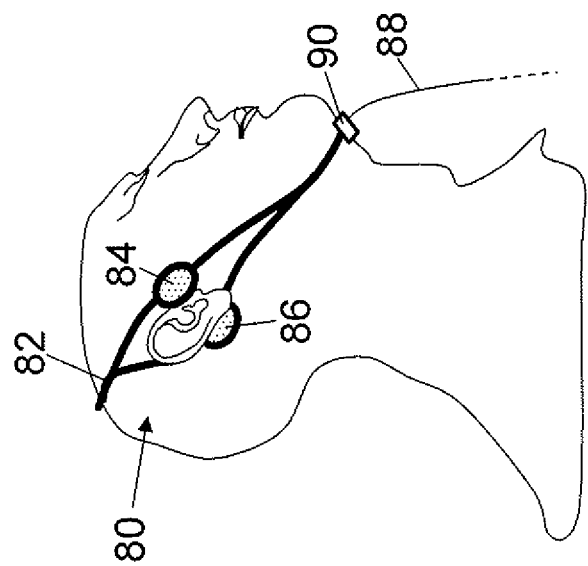

FIG. 13 diagrammatically shows a core body temperature measurement device including a mechanical frame in the form of a circumferential headband.

Figure 14:
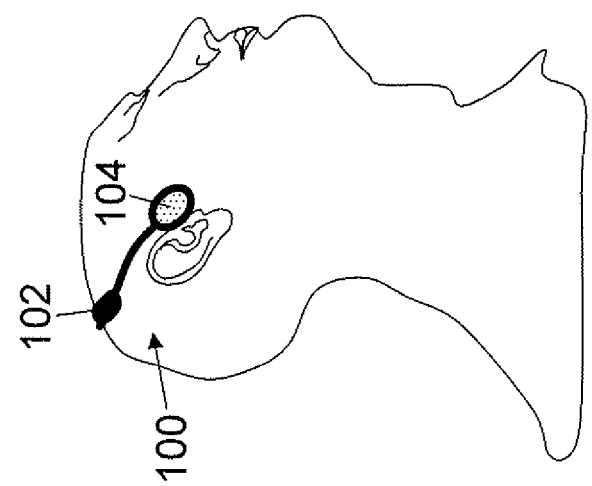

FIG. 14 diagrammatically shows a core body temperature measurement device including a mechanical frame in the form of a generally hemispherical headband.

Figure 15:
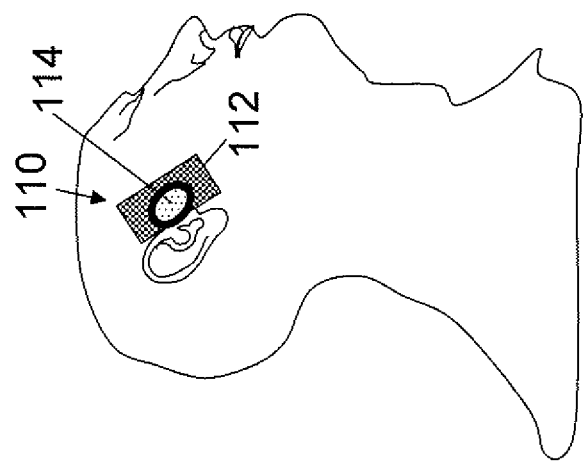

FIG. 15 diagrammatically shows a core body temperature measurement device including a mechanical frame in the form of an adhesive pad.

Figure 16:
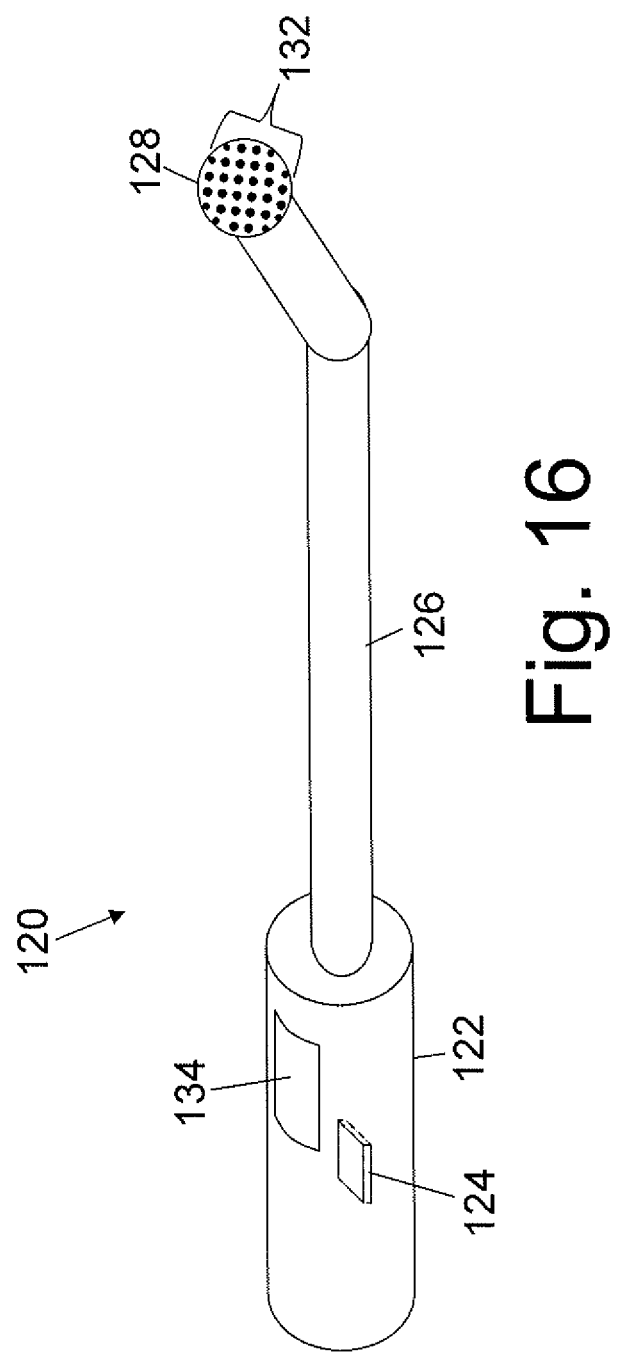

FIG. 16 diagrammatically shows an oral thermometer including a plurality of electronic temperature sensors.

With reference to FIGS. 1 and 2, as used herein core body temperature is taken to correspond to the brain temperature. It is advantageous to measure core body temperature at a surface having a surface temperature approximating the core body temperature. For example, Abreu U.S. Published Application 2004/0059212, discloses measuring core body temperature at a thermally conductive pathway to the brain, called a "brain tunnel" in US 2004/0059212, located between the eyes proximate to an orbit or eye socket. This location is indicated in FIGS. 1 and 2 as the "between-the-eyes" location BTT. Another previously identified surface having a surface temperature approximating the core body temperature is the sublingual pocket (not visible in FIGS. 1 and 2) inside of the mouth. A posterior or rear of a sublingual pocket has been found to have a surface temperature approximating the core body temperature.

With continuing reference to FIGS. 1 and 2, it is recognized herein that skin overlaying arterial blood-rich superficial regions disposed near an auricle define other surfaces having a surface temperature approximating the core body temperature. The auricle, also known as the pinna, is the outer, projecting portion of the ear, that is, the visible part of the ear that resides outside of the head. The superficial temporal artery is positioned forward of the auricle and carries arterial blood from the external carotid artery outward toward the surface of the scalp in front of the auricle. Accordingly, a temperature measurement device may be operatively coupled with skin overlaying a portion of a superficial temporal artery disposed anterior (that is, in front of) the auricle, such as at a region STA indicated in FIGS. 1 and 2. As another example, arterial vessels disposed behind the auricle, such as the posterior auricular artery, carry arterial blood from the external carotid artery outward toward the surface of the scalp behind the ear. Accordingly, a temperature measurement device may be operatively coupled with skin overlaying a portion of an artery ascending posterior to (that is, behind) the auricle, such as at the region PAA indicated in FIGS. 1 and 2.

While FIGS. 1 and 2 show the configuration of the aforementioned arteries, auricle, and other anatomical features for the right auricle, it is to be understood that bilateral symmetry pertains, and similar core body temperature measurement positions exist for the left auricle as well. Indeed, in some embodiments core body temperature measurements are acquired from regions disposed near both the left and right auricles.

With reference to FIG. 3, a suitable readout controller 10 for a core body temperature measurement device is described. The readout controller 10 reads temperature measurements using an electronic temperature sensor or, in some embodiments, a plurality of electronic temperature sensors 12, that are thermally coupled with a surface having a surface temperature approximating the core body temperature. For example, the electronic temperature sensors 12 may be coupled with the region STA of FIGS. 1 and 2, the region PAA of FIGS. 1 and 2, the region BTT of FIGS. 1 and 2, the sublingual pocket inside the mouth (not shown in FIGS. 1 and 2), or some combination of these locations. An advantage of providing the plurality of temperature sensors 12, rather than a single temperature sensor, is that the plurality of temperature sensors 12 can sample different portions of the skin or other surface. The precise location of the region STA, region PAA, region BTT, the sublingual pocket, or so forth, may vary from person to person and may be difficult to locate precisely on a given subject.

Using the plurality of temperature sensors 12 accommodates such individual variation. A maximum reading selector 14 selects the highest temperature measurement acquired by the plurality of temperature sensors 12 as a highest usable temperature reading 15 for determining the core body temperature. This approach relies on the recognition made herein that the measured temperature should be highest at that point where the skin temperature most closely approximates the core body temperature. Lower temperature measurements generally reflect higher thermal losses away from the surface having a surface temperature approximating the core body temperature. Lower temperature measurements may also reflect inaccurate temperature readings due to poor thermal contact of the temperature sensor with the skin or other measurement errors. Thus, by using the plurality of temperature sensors 12 and employing the maximum reading selector 14 to select the highest temperature measurement, such difficulties are alleviated.

With brief reference to FIGS. 4-6, in some embodiments the maximum temperature reading selector 14 uses a more complex algorithm for determining the highest usable temperature from which the core body temperature is determined. FIG. 4 shows an embodiment of the maximum reading selector 14 that includes an interpolator 14a for spatially interpolating the acquired temperature readings, and a peak detector 14b for identifying the peak interpolated temperature as the highest usable temperature reading 15.

FIGS. 5 and 6 illustrate this approach further. FIG. 5 shows an example surface thermal profile of the skin surface at and near to the "brain tunnel" BTT. In FIG. 5, the surface thermal profile is indicated by grayscale shading, with darker shading corresponding to higher temperature. The dark central position of the surface thermal profile corresponds to the center of the "brain tunnel" BTT, where the surface temperature is closest to the core body temperature. At positions increasingly further away from the "brain tunnel" BTT, there is generally more thermal loss across intervening tissue such as skin or fat, resulting in a lower surface temperature. The plurality of temperature sensors 12 in FIG. 5 comprises a 6×7 rectangular array, with each temperature sensor diagrammatically indicated in FIG. 5 by a filled circle. Arrays with other numbers of sensors, and optionally arranged in other ways, are also contemplated.

FIG. 6 plots a two-dimensional interpolated temperature surface $T_S(x,y)$ generated by the interpolator 14a from the temperature readings acquired by the plurality of temperature sensors 12 positioned respective to the brain tunnel location BTT as shown in FIG. 5. The interpolation may be done using a piece-wise constant interpolation algorithm, a piece-wise linear interpolation algorithm, a piece-wise quadratic interpolation algorithm, a higher-order interpolation algorithm, or so forth. The peak detector 14b suitably determines the highest usable temperature $T_{max}$ as the value of the interpolated temperature surface $T_S(x,y)$ at which the gradient $\nabla T_S$ of the two-dimensional temperature surface goes to zero. That is, the peak detector 14b determines $T_{max}=T_S(x_o,y_o)$ where $\nabla T_S|_{(x_o,y_o)}=0$.

With returning reference to FIG. 4 and with further reference to FIGS. 7 and 8, if the peak detector 14b fails to identify a peak at which the derivative or gradient goes to zero, this may indicate that the plurality of temperature sensors 12 does not encompass the "brain tunnel" BTT or other maximum temperature point on the surface where the surface temperature most closely approximates the core body temperature. In FIG. 7, the array of temperature sensors 12 is positioned too far to the left of the brain tunnel BTT, such that it does not encompass the brain tunnel BTT. FIG. 8 shows the corresponding interpolated temperature surface $T_S(x,y)$, which in this case does not have any peak at which $\nabla T_S$ goes to zero. Thus, the peak detector 14b outputs a "no peak" result 14c which is suitably used to issue an error warning 14d. Optionally, "no peak" result 14c includes an indication of the position of the highest temperature of the interpolated temperature surface $T_S(x,y)$, and the error warning 14d includes a suggestion to move the temperature measurement device in the direction of the position of highest temperature. In the illustrative example of FIGS. 7 and 8, the highest temperature is at the right of the array of temperature sensors 12, and so the error warning 14d would suggest moving the temperature measurement device to the right.

On the other hand, if multiple peaks are located (that is, if $\nabla T_S=0$ at more than one position) then the highest interpolated temperature of the multiple peaks is suitably defined as $T_{max}$. For example, if $\nabla T_S(x_1,y_1)=0$ and $T_S(x_1,y_1)=37.4°$ C., while $\nabla T_S(x_2,y_2)=0$ and $T_S(x_2,y_2)=37.1°$ C., then selection of $T_{max}=37.4°$ C. is appropriate.

In the embodiments described with reference to FIGS. 5-8, the plurality of temperature sensors 12 is arranged two-dimensionally. In other embodiments, the plurality of temperature sensors 12 may have a linear, curvilinear, or other one-dimensional arrangement. In such embodiments, the interpolator 14a suitably generates an interpolated one-dimensional temperature-versus position curve (e.g., $T_S(x)$) rather than the two-dimensional surface $T_S(x,y)$, and the gradient $\nabla T_S$ for such a one-dimensional curve has the form of a one-dimensional derivative (e.g., $\nabla T_S=dT_S/dx$).

Still further, the maximum reading selector 14a, 14b illustrated in FIG. 4 is an example. In another suitable embodiment, the maximum reading selector 14 determines the maximum usable temperature as the maximum temperature reading acquired by any of the temperature sensors 12, except that any temperature above an outlier threshold is discarded. For example, the outlier threshold may be set at 43° C., since a temperature reading that high is not likely to be physically correct for a living human subject. This approach advantageously omits from consideration any unrealistic or non-physical temperature readings, such as might result from a malfunctioning temperature sensor of the plurality of temperature sensors 12. Such outlier exclusion can also be used in conjunction with the maximum temperature reading selector 14a, 14b of FIG. 4. Although the approach using the plurality of temperature sensors 12 has advantages, it is also contemplated to employ a single temperature sensor to acquire a single temperature measurement, and to omit the maximum reading selector 14.

With returning reference to FIG. 3, a temperature corrector 16 optionally increases the highest usable temperature reading 15 to account for a temperature drop across the skin, so as to more accurately determine the core body temperature. Alternatively, such a correction can be made to the temperature readings acquired by the plurality of temperature sensors 12 before input to the maximum temperature reading selector 14. In one approach, this correction is made by adding a fixed amount, such as 1° C., to the highest usable temperature reading 15 to provide an estimated correction for the temperature drop due to thermal losses in the skin. This approach is computationally straightforward, but can lead to some error since the actual skin temperature drop varies based on factors such as moisture (e.g., sweat), ambient temperature, air convection, and so forth. More computationally elaborate skin temperature drop corrections can be used, as described later herein. Moreover, the temperature corrector 16 can correct for other factors that may affect the accuracy of the core body temperature measurement. For example, if the electronic temperature sensors 12 are thermocouples, the temperature corrector 16 may include a correction for non-linearity of the temperature-versus-thermocouple voltage characteristic. The output of the temperature corrector 16 is the core body temperature.

Optionally the temperature measurement device includes sensors to acquire other physiological parameters besides temperature. For example, a blood oxygen sensor 20, such as an $SpO_2$ sensor or an $StO_2$ sensor, acquires a measurement (typically an optically based measurement in the case of an $SpO_2$ or $StO_2$ sensor) that is converted into a blood oxygenation level reading and a pulse reading by a pulse/oxygen extractor 22. Different or additional sensors can be included, such as a blood pressure sensor.

The resulting information including the core body temperature and optional other readings such as blood oxygenation and pulse are output by a suitable output path such as a built-in display (not shown in FIG. 3), a wired connection, an illustrated wireless transmitter 24 or transceiver that outputs a wireless data signal 26, or so forth. The core body temperature measurement device optionally includes other features. For example, if the core body temperature data is offloaded from the temperature measurement device using a wired connection, then the wired connection can incorporate a power input lead to power the sensors 12, 20 and processor 10. Alternatively, if the illustrated wireless transmitter 24 or transceiver is used such that the core body temperature measurement device is a wireless device, then an on-board battery 28, power capacitor, or other on-board electrical power supply is suitably included.

As mentioned previously, the optional skin temperature corrector 16 in some embodiments employs an estimated skin temperature drop correction, such as a 1° C. temperature drop correction. This approach is computationally straightforward, but can lead to some error since the actual skin temperature drop varies based on factors such as moisture (e.g., sweat), ambient temperature, air convection, and so forth. To accommodate such factors, in some embodiments the skin temperature corrector 16 employs a more complex corrective approach based on feedback. Some suitable temperature correction algorithms are disclosed in Fox et al., U.S. Pat. No. 3,933,045 which is incorporated herein by reference; Heikkilä et al, U.S. Pat. No. 5,816,706 which is incorporated herein by reference; and Tokita et al., U.S. Pat. No. 6,886,978 which is incorporated herein by reference.

One suitable temperature correction algorithm operates in conjunction with the one or more skin temperature sensors 12 each configured to include parallel conductive plates or films spaced apart by a distance that is adjustable using inchworm actuators, MEMS actuators, or so forth. These temperature sensors are in effect combination temperature/heat flux sensors, because by acquiring temperature measurements across the two plates at different plate separations, the heat flux can be determined, from which the skin temperature drop can in turn be estimated. Designating the temperatures of the two conductive plates as $T_1$ and $T_2$, respectively, and the core body temperature as $T_{core}$, the following expression holds:

$$\frac{dT}{dt} = \alpha \frac{d^2 T}{dx^2}, \quad (1)$$

where $\alpha = \lambda/\rho c_P$, $\lambda$ denotes thermal conductivity, $\rho$ denotes density, and $c_P$ denotes specific heat. In a suitable coordinate system, x denotes depth with x=0 corresponding to a point inside the body at temperature $T_{core}$ and $x=h_s$ corresponding to the surface of the skin. The boundary conditions for Equation (1) include the core body temperature $T_{core}$ (to be determined) at x=0, and the measured temperature $T_s$ at $x=h_s$, that is, at the surface of the skin. If the conductive plate at temperature $T_2$ is contacting or otherwise in good thermal communication with the skin, then $T_s=T_2$ to a good approximation. The heat flux out of the skin is denoted $q_s$ herein.

Assuming the skin 33 can be represented as a plane of thickness $h_s$ and thermal conductivity $\lambda_s$, the heat flux out of the skin $q_s$ (that is, heat transfer rate on a per-unit area basis) can be written as:

$$q_s = -\lambda \frac{dT}{dx} \text{ at } x = h_s, \quad (2)$$

and a solution of Equation (1) can be approximated as:

$$T_{core} = T_s + \frac{h_s}{\lambda_s} q_s + \frac{h_s^2}{2\alpha_s} \frac{dT_s}{dt}. \quad (3)$$

At equilibrium, Equation (3) reduces to:

$$T_{core} = T_s + \frac{h_s}{\lambda_s} q_s, \quad (4)$$

which demonstrates that the core body temperature $T_{core}$ is higher than the skin temperature by a temperature drop across the skin corresponding to $(h_s/\lambda_s) \cdot q_s$.

By using feedback control of actuators separating the parallel conductive plates or films, the values of the quantities $T_s$, $q_s$, and $$\frac{dT_s}{dt}$$

can be measured for different moments in time $t_i = \{t_1, \ldots, t_n\}_{to}$ produce a matrix of coupled equations:

$$\begin{bmatrix} 1 & -\xi_1 & -\eta_1 \\ & \cdots & \\ 1 & -\xi_n & -\eta_n \end{bmatrix} \begin{bmatrix} T_{core} \\ \frac{h_s}{\lambda_s} \\ \frac{h_s^2}{2\alpha_s} \end{bmatrix} = \begin{bmatrix} T_s(t_1) \\ \vdots \\ T_s(t_n) \end{bmatrix}, \quad (5)$$

in which the unknown quantities are $T_{core}$, $$\frac{h_s}{\lambda_s} \text{ and } \frac{h_s^2}{2\alpha_s},$$

and where:

$$\xi \equiv q_s(t_i), \quad (6)$$
and
$$\eta \equiv \frac{dT_s}{dt}(t_i). \quad (7)$$

It is assumed here that $T_{core}$, $$\frac{h_s}{\lambda_s} \text{ and } \frac{h_s^2}{2\alpha_s}$$

are time-independent during the time interval $\{t_1, \ldots, t_n\}$ over which the set of measurements are acquired. The system of Equations (5) can be solved by the temperature corrector 16 using a least squares minimisation procedure or other suitable coupled equations solver to provide the body core temperature $T_{core}$, and also the heat flux $q_s$ through the surface of the skin. The sampling moments $t_i$ are suitably chosen such that to ensure that the system of Equations (5) is well-conditioned.

In some embodiments, the heat flux across the parallel conductive plates of a parallel-plate temperature/heat flux sensor is determined by a combination of thermal and electrical measurements. This approach makes use of a formal correspondence identified herein between the electrostatic potential distribution given by Poisson's equation ($\in \cdot \nabla^2 \phi = 0$) and the expression for temperature distribution ($k \cdot \nabla^2 T = 0$). Comparing these equations and using the boundary conditions $\phi|_{\Omega_1} = \phi_1$ and $T|_{\Omega_1} = T_1$ at the conductive plate arranged distal from the skin having a surface designated $\Omega_1$ and $\phi|_{\Omega_2} = \phi_2$ and $T|_{\Omega_2} = T_2 = T_s$ at the conductive plate contacting the skin having a surface designated $\Omega_2$, it can be shown that $$\eta_T = \left(\frac{k}{\varepsilon}\right) \cdot C,$$

where $\eta_T$ is the thermal conductance between the two spaced-apart conductive plates, C is the mutual capacitance of the two spaced-apart conductive plates, k is the thermal conductivity of the dielectric material spacing apart the conductive plates, and $\in$ is the dielectric constant of the dielectric material spacing apart the conductive plates. In deriving this relationship between thermal conductance $\eta_T$ and mutual capacitance C, it is assumed that the ratio $k/\in$ is a constant. This assumption holds sufficiently for air, foam, polyethylene, and numerous other common dielectric spacers. The dielectric constant or permittivity $\in$ of the dielectric spacer is related to the vacuum permittivity $\in_o \approx 8.8542 \times 10^{-12}$ F/m by the relative dielectric constant $\in_r$ according to the relationship $\in = \in_r \cdot \in_o$.

FIG. 9 shows a suitable temperature/heat flux sensor making use of this capacitance/thermal conductance relationship. Two conductive plates 30, 31 are spaced apart by a dielectric material 32. The conductive plate 31 is in thermal contact with skin 33. Actuators 34 such as piezoelectric elements, inchworm elements, or so forth, enable electrically driven control of the separation of the conductive plates 30, 31. In this embodiment, the temperatures $T_1$, $T_2$ of the respective conductive plates 30, 31 are measured by respective thermocouples 35, 36 or other suitable temperature transducers, and the mutual capacitance C of the plates 30, 31 is measured by a capacitance meter 37. The temperatures $T_1$, $T_2$ and the mutual capacitance C for each of the temperature sensors 12 is input to the controller 10, where the temperature corrector 16 is configured to apply the temperature correction set forth referencing Equations (1)-(7) and making use of the heat flux $$f = (T_1 - T_2) \cdot \eta_T = (T_1 - T_2) \cdot \left(\frac{k}{\varepsilon}\right) \cdot C.$$

The relationship $$\eta_T = \left(\frac{k}{\varepsilon}\right) \cdot C$$

enables the heat flux f across the parallel plates 30, 31 to be determined for the known (measured) $T_1$ and $T_2$ by a straightforward mutual capacitance measurement using a capacitance meter, from which the heat flux across the skin can be estimated. Advantageously, the geometrical assumptions going into derivation of the relationship $$\eta_T = \left(\frac{k}{\varepsilon}\right) \cdot C$$

are limited—for example, spaced apart conductive bodies that are not parallel plates can be used. In the combination temperature/heat flux sensor of FIG. 9, for example, the conductive plate 30 includes a a pin or other protrusion 38 that decreases the plate separation distance and increases measurement sensitivity. Alternatively, one or more such pins or protrusions can be included on the plate 31, or on both plates 30, 31.

As another approach, the temperature corrector 16 can make a skin temperature drop correction determined based on physiological measurements such as the ambient temperature (suitably acquired using a temperature sensor that is not in contact with or close to the skin), skin sheet resistance or conductivity (measurable using a first electrode pair driving a small current and a second electrode pair measuring voltage generated by the drive current), or so forth. A lookup table or empirical formula suitably relates the skin temperature drop correction to the measured ambient temperature, skin sheet resistance, or other parameters.

In some contemplated embodiments of the temperature corrector 16, the corrective approach of Tokita et al, U.S. Pat. No. 6,886,978 is used, in which a variable heater provides a perturbation of the temperature distribution from which the core body temperature can be estimated. In this approach, the temperature distribution can be written for the sensor of FIG. 9 as $(dT_2/dx) = a \cdot (T_{core} - T_2) - b \cdot (T_2 - T_1)$ where a and b are constants and $T_{core}$ is the core body temperature. This relationship is derived in Tokita (note that the notation of Tokita reverses $T_1$ and $T_2$ versus FIG. 9). The sensor of FIG. 9 is used to acquire the data set $(T_1, T_2, dT_2/dx)$ for several different heating levels provided by the variable heater, producing a set of equations that can be solved simultaneously to obtain the parameters a, b, and $T_{core}$. In some suitable embodiments, an optical source 22a of the blood oxygen sensor 20 provides variable heating for this purpose. For example, a $SpO_2$ sensor typically includes a semiconductor laser, LED, or other optical source for acquiring the $SpO_2$ reading—the optical source can also be operated at different power levels to provide variable heating for core body temperature measurement using the sensor of FIG. 9 and the skin temperature drop correction as set forth in Tokita. In some such embodiments, the sensor of FIG. 9 is modified by omission of the pin 38, so that a well-defined planar geometry is provided. In other embodiments, the pin 38 is retained along with the capacitance meter 37, and the relation $$\eta_T = \left(\frac{k}{\varepsilon}\right) \cdot C$$

is used to derive the heat flux between the plates 30, 31 from which along with $T_1$ and $T_2$ the derivative $dT_2/dx$ is determined Additionally, the actuators 34 can be omitted in these embodiments in which thermal (i.e., heating) perturbation is used instead of mechanical perturbation. With the actuators 34 omitted, the spacing of the conductive layers or plates 30, 31 is not modifiable.

With reference to FIGS. 10-15, several head-mountable mechanical frames are set forth as illustrative examples of ways of mounting temperature sensor arrays to one or both of the surfaces STA, PAA shown in FIGS. 1 and 2 and having surface temperature approximating the core body temperature. The use of a head mountable mechanical frame facilitates extended monitoring of core body temperature.

FIG. 10 diagrammatically shows a core body temperature measurement device 40 including a mechanical frame in the form of an eyeglasses frame 42. The eyeglasses frame 42 can contain prescriptive lenses for correcting eyesight, or can contain non-corrective lenses, or can have no lenses at all. A first set of temperature sensors 12f are mounted near the left and right bends of the frame and are operatively coupled with skin overlaying portion of the superficial left and right temporal arteries anterior to the left and right auricles. A second set of temperature sensors 12b are mounted near the left and right earpieces and are operatively coupled with skin overlaying portions of left and right arteries ascending posterior to the left and right auricles. The temperature sensors 12f, 12b are mounted on supports 44 that each include a spring bias 46 coupling the support to the eyeglasses frame and pressing the supported temperature sensors against the skin overlaying the target arterial blood-rich superficial region. The readout controller is suitably embodied by microchips 48 disposed on the eyeglasses frame 42 as illustrated. Wired connections 50 provide power to the microchips 48 and sensors 12f, 12b and provide a pathway for offloading the acquired core body temperature measurements and optional blood oxygenation or other measurements. A wireless implementation of the described solution is also contemplated.

FIG. 11 diagrammatically shows a core body temperature measurement device 60 including a mechanical frame in the form of a behind-the-head pillow 62 having extensions 64 configured to loop over the left and right auricles (only the right-side extension 64 is visible in FIG. 11). One or more temperature sensors are mounted on one or more supports 66 disposed on one or both extensions 64. Optionally, a microchip 68 defining the readout controller 10 is disposed on or in the behind-the-head pillow 62 and operatively connects with the temperature sensors on the supports 66 via wires (not shown) running inside of or along the extensions 64.

FIG. 12 diagrammatically shows a core body temperature measurement device 70 including a mechanical frame in the form of headset including an earloop 72 disposed around a proximate auricle without a headband. The illustrated embodiment includes a first temperature sensor support 74 disposed anterior to the right auricle and coupling one or more temperature sensors with skin overlaying a portion of the right superficial temporal artery, and a second temperature sensor support 76 disposed posterior to the right auricle and coupling one or more temperature sensors with skin overlaying a portion of an artery ascending posterior to the right auricle. The illustrated core body temperature measurement device 70 is a wireless device, and accordingly includes the readout controller 10 (FIG. 3) with the on-board battery 28 or other on-board power source and wireless transmitter 24 or transceiver mounted on the earloop 72. Some suitable on-board power devices and transmitters are known and used in existing wireless Bluetooth headsets that are sometimes embodied as earloops.

FIG. 13 diagrammatically shows a core body temperature measurement device 80 including a mechanical frame in the form of a circumferential headband 82 with one or more supports for one or more temperature sensors disposed on the circumferential headband proximate to one or both auricles and contacting skin overlaying one or more arterial blood rich superficial regions disposed near the proximate auricle or auricles. In the illustrated embodiment, a front support 84 is disposed anterior to the right auricle and couples one or more temperature sensors with skin overlaying a portion of the right superficial temporal artery, and a back temperature sensor support 86 is disposed posterior to the right auricle and couples one or more temperature sensors with skin overlaying a portion of an artery ascending posterior to the right auricle. Optionally, corresponding supports for temperature sensors are also provided proximate to the left auricle. A wired connection 88 extends from an under-the-chin readout controller 90 for offloading core body temperature measurements and optionally other measurements, and for supplying electrical power to the device 80. The under-the-chin readout controller 90 suitably has a configuration similar to that of the controller of FIG. 3.

FIG. 14 diagrammatically shows a core body temperature measurement device 100 including a mechanical frame in the form of a generally hemispherical headband 102 having an end with a temperature sensor support 104 disposed anterior to the right auricle and coupling one or more temperature sensors with skin overlaying a portion of the right superficial temporal artery. The readout controller is suitably mounted on top of the hemispherical head 102 (not shown in the perspective view of FIG. 14) and optionally includes the wireless transmitter 24 or transceiver.

FIG. 15 diagrammatically shows a core body temperature measurement device 110 including a mechanical frame in the form of an adhesive pad 112 adhered to contact skin overlaying a portion of the right superficial temporal artery. One or more temperature sensors are suitably disposed on, under, or in the adhesive pad 112 in thermal communication with the skin. In the illustrated embodiment, a rigid disk 114 contains the one or more temperature sensors along with a readout controller suitably conforming with the readout controller 10 of FIG. 3.

The mechanical frames illustrated in FIGS. 10-15 are examples. Other head-mounted mechanical frames may be used that are configured to operatively couple one or more temperature sensors with a surface having a surface temperature approximating the core body temperature. For example, some of the mechanical frames shown in Abreu, U.S. Published Application 2004/0059212 for coupling a temperature sensor with the "brain tunnel" BTT of Abreu are readily adapted to support an array or other plurality of temperature sensors.

With reference to FIG. 16, the core body temperature measurement approaches disclosed herein may be practiced in other ways besides through the use of a head-mountable mechanical frame. For example, FIG. 16 shows a hand-held oral thermometer 120 having a body that includes a handle 122 containing a microchip 124 or other element or combination of elements embodying the controller 10 (see FIG. 3), a neck 126, and a generally spherical sensors head 128 supporting an array or other plurality of sensors 132. The handle 122 and neck 126 enable a physician, nurse, or other person to insert the generally spherical sensors head 128 into a subject's mouth, preferably in a sublingual pocket inside of the mouth, and more preferably in a posterior or rear region of a sublingual pocket inside of the mouth. The temperature readout from the controller 10 is suitably displayed via a built-in LCD display 134, or can be offloaded from the thermometer 120 via a wireless or wired connection (not shown in FIG. 16).

The provision of a plurality of temperature sensors 132 (represented by filled circles in FIG. 16) distributed over the generally spherical sensors head 128, along with a suitable implementation of the maximum temperature reading selector 14 in the controller 10, substantially improves the likelihood that an accurate temperature reading will be obtained even if there is substantial mispositioning of the generally spherical sensors head 128 in the sublingual pocket. The combination of a plurality of temperature sensors 132 and the maximum temperature reading selector 14 also provides robustness against individual anatomical variations that may result in unusual subject-specific arterial configurations proximate to the sublingual pocket, or unusual subject-specific sublingual pocket geometries. For the purposes of temperature interpolation, the spatial arrangement of the plurality of temperature sensors 132 is suitably represented as a surface in a spherical coordinates system, or as a Cartesian surface approximately wrapped around the generally spherical sensors head 128, or the like. Because some of the spherical area is occupied by the connection of the neck 126 to the generally spherical sensors head 128, the plurality of temperature sensors 132 generally do not span an entire sphere. Moreover, it is contemplated for the generally spherical sensors head 128 to be ellipsoidal or otherwise-shaped.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A physiological sensor device for measuring core body temperature of a subject, the physiological sensor device comprising:
a plurality of electronic temperature sensors wherein each electronic temperature sensor includes a first conductive body arranged to be placed in thermal contact with a surface having a surface temperature approximate the core body temperature of the subject and a second conductive body spaced apart from the first conductive body and the surface by a dielectric disposed between the first and second conductive bodies, a first temperature sensor configured to measure the temperature of the first conductive body, a second temperature sensor configured to measure the temperature of the second conductive body, actuators configured to control separation of the spaced-apart first and second conductive bodies, a capacitance meter configured to measure mutual capacitance of the spaced-apart first and second conductive bodies with the dielectric disposed between the first and second conductive bodies; and
a readout controller comprising a microchip configured to, for each electronic temperature sensor:
receive measurements of the respective temperatures of the spaced-apart first and second conductive bodies from the first and second temperature sensors and measurement of a mutual capacitance of the spaced apart first and second conductive bodies from the capacitance meter for a plurality of different separations of the spaced-apart first and second conductive bodies controlled using the actuators,
estimate a skin temperature drop based on received measurements of the respective temperatures of the spaced-apart first and second conductive bodies and of the mutual capacitance at the different separations of the spaced-apart first and second conductive bodies, and
correct the received temperature of the first conductive body for the estimated skin temperature drop to generate a temperature reading from the electronic temperature sensor, wherein the readout controller is further configured to output a core body temperature based on a highest usable temperature reading of the acquired temperature readings.

2. The physiological sensor device as set forth in claim 1, wherein the plurality of electronic temperature sensors are configured to be operatively coupled with said surface selected from the group consisting of: (i) skin overlaying a portion of a superficial temporal artery disposed anterior to an auricle, (ii) skin overlaying a portion of an artery ascending posterior to an auricle, and (iii) a brain tunnel between the eyes.

3. The physiological sensor device as set forth in claim 1, further comprising:
a head mountable mechanical frame or pad configured to operatively couple the electronic temperature sensors with said surface having a surface temperature approximating the core body temperature.

4. The physiological sensor device as set forth in claim 1, wherein the readout controller is configured to identify the highest usable temperature reading of the acquired temperature readings by
spatial interpolation of temperature readings of the plurality of electronic temperature sensors to generate an interpolation; and
detection of the highest usable temperature reading of the acquired temperature readings as a peak of the interpolation.

5. The physiological sensor device as set forth in claim 4, wherein the interpolation is one of (i) a two dimensional interpolated temperature surface and (ii) a one dimensional interpolated temperature versus position curve.

6. A core body temperature measurement device for measuring core body temperature of a subject, the core body temperature measurement device comprising:
spaced-apart first and second conductive bodies configured to be arranged with the first conductive body in thermal contact with a surface having a surface temperature approximate the core body temperature of the subject and the second conductive body spaced apart from the first conductive body and the surface by a dielectric disposed between the first and second conductive bodies;
a first temperature sensor configured to measure the temperature of the first conductive body;

a second temperature sensor configured to measure the temperature of the second conductive body;

actuators configured to control separation of the spaced-apart first and second conductive bodies;

a capacitance meter configured to measure mutual capacitance of the spaced-apart first and second conductive bodies with the dielectric disposed between the first and second conductive bodies; and a controller comprising a microchip configured to:
(i) receive measurements of the respective temperatures of the spaced-apart first and second conductive bodies from the first and second temperature sensors,
(ii) receive measurement of a mutual capacitance of the spaced apart first and second conductive bodies from the capacitance meter,
(iii) repeat operations (i) and (ii) for a plurality of different separations of the spaced-apart first and second conductive bodies controlled using the actuators,
(iv) estimate a skin temperature drop based on received measurements of the respective temperatures of the spaced-apart first and second conductive bodies and of the mutual capacitance at the different separations of the spaced-apart first and second conductive bodies;
(v) correct the received temperature of the first conductive body for the estimated skin temperature drop to generate a measurement of the core body temperature.

7. The core body temperature measurement device as set forth in claim 6, wherein the core body temperature measurement device is configured to be operatively coupled with said surface selected from the group consisting of: skin overlaying a portion of a superficial temporal artery disposed anterior to an auricle, skin overlaying a portion of an artery ascending posterior to an auricle, a brain tunnel between the eyes; and a sublingual pocket inside of a mouth.

8. The core body temperature measurement device as set forth in claim 6, comprising a head mountable mechanical frame or pad configured to place the first conductive body in thermal contact with said surface.

9. A core body temperature measurement device for measuring core body temperature of a subject, the core body temperature measurement device comprising:

a first conductive body arranged to be placed in thermal contact with a surface having a surface temperature approximate the core body temperature of the subject;

a second conductive body spaced apart from the first conductive body and the surface by a dielectric disposed between the first and second conductive bodies;

actuators configured to control separation of the spaced-apart first and second conductive bodies;

temperature sensors configured to measure temperature of the first conductive body and to measure temperature of the second conductive body;

a capacitance meter configured to measure mutual capacitance of the spaced-apart first and second conductive bodies with the dielectric disposed between the first and second conductive bodies; and a readout controller comprising a microchip, the readout controller configured to:
(i) estimate a skin temperature drop based on mutual capacitance
of the spaced-apart first and second conductive bodies measured by the capacitance meter and temperatures of the first and second conductive bodies measured by the temperature sensors at different separations of the spaced-apart first and second conductive bodies; and
(ii) correct the measured temperature of the first conductive body for the estimated skin temperature drop to generate a measurement of the core body temperature.

10. The core body temperature measurement device of claim 9 wherein the actuators include piezoelectric, inchworm, or MEMS actuators configured to control separation of the spaced-apart first and second conductive bodies.

11. The core body temperature measurement device of claim 9 wherein the temperature sensors include:
a first thermocouple configured to measure temperature of the first conductive body; and
a second thermocouple configured to measure temperature of the second conductive body.

12. The core body temperature measurement device of claim 9 wherein at least one of the first conductive body and the second conductive body includes a protrusion extending toward the other of the first conductive body and the second conductive body.

* * * * *